United States Patent [19]

Schut et al.

[11] 4,283,336
[45] Aug. 11, 1981

[54] PROCESS FOR THE PREPARATION OF 3-AMINO-2-(5-FLUORO AND 5-METHOXY-1H-INDOL-3-YL)PROPANOIC ACID DERIVATIVES

[75] Inventors: Robert N. Schut, Edwardsburg, Mich.; Max E. Safdy, Elkhart, Ind.; Enrique Hong, Mexico City, Mexico

[73] Assignee: Miles Laboratories, Inc., Elkhart, Ind.

[21] Appl. No.: 85,915

[22] Filed: Oct. 17, 1979

Related U.S. Application Data

[62] Division of Ser. No. 915,735, Jun. 15, 1978, abandoned.

[51] Int. Cl.³ .................. C07D 209/18; C07D 209/20
[52] U.S. Cl. .................. 260/326.14 R; 260/326.14 T; 260/326.13 B
[58] Field of Search .............. 260/326.14 R, 326.13 B, 260/326.14 T

[56] References Cited

PUBLICATIONS

Roshkov et al, J. of Org. Chem. of USSR, 12, 1976, pp. 1076–1079, (Translation pp. 1087–1089).

*Primary Examiner*—Donald G. Daus
*Assistant Examiner*—D. B. Springer
*Attorney, Agent, or Firm*—Jerome L. Jeffers

[57] ABSTRACT

The compounds having Formula I,

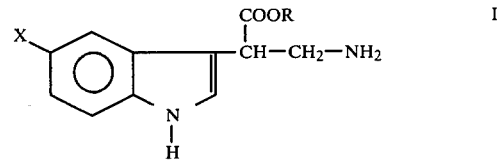

wherein X is a fluorine or methoxy group, and R is a hydrogen or methyl group, such that R is hydrogen only when X is fluorine are novel. The compounds having Formula I and their acid addition salts are useful for the treatment of hypertension. Processes for the preparation of the compounds having Formula I and useful intermediates are described.

5 Claims, No Drawings

PROCESS FOR THE PREPARATION OF 3-AMINO-2-(5-FLUORO AND 5-METHOXY-1H-INDOL-3-YL)PROPANOIC ACID DERIVATIVES

This is a division of application Ser. No. 915,735, filed June 15, 1978, now abandoned.

BACKGROUND AND PRIOR ART

Tryptophan, an essential amino acid nutrient having the formula:

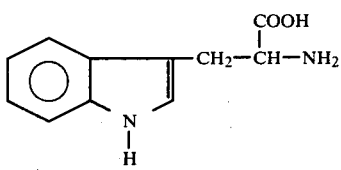

is converted in part by the body into serotonin and melatonin. This later named compound possesses central nervous system activity. Another metabolite of tryptophan, 5-hydroxytryptophan, has been reported by Antonaccio and Robson (J. Pharm. Pharmacol. 25, 495 [1973]) to cause a decrease in blood pressure in monoamine oxidase-inhibited dogs. Another tryptophan derivative, α-methyl-5-hydroxytryptophan, has been reported to lower blood pressure in spontaneously hypertensive rats when given at the extremely large dose of 200 mg/kg (Tabei et al., Eur. J. Pharmacol., 7, 39 [1969]). 5-Fluorotryptophan has been reported to interfere with the synthesis of indole from anthranilic acid and inhibit the growth of E. coli (Bergmann, Proc. Konig. Ned. Akad. Wetenschap, Series C, 57, 108 [1954]).

Rozhkov et al. (Zh. Org. Khim. 12[5], 1076 [1976]) have synthesized the structural isomer of tryptophan, having the structure:

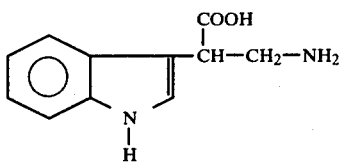

Rozhkov et al. state no utility for this compound.

Johnson et al have reported that the corresponding α,β-dehydro compound:

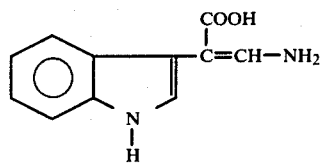

is useful as a chromophore intermediate (Biolumin. Progr. Proc. Kanagawa-ken, Jap. 1965, 67; Chem. Abst. 67;53994K [1967]).

SUMMARY OF THE INVENTION

The subject matter of this invention includes:
(1) A compound having the structural Formula I:

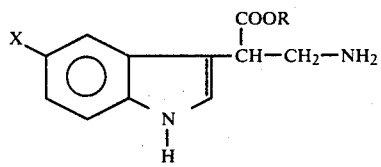

wherein R is a hydrogen or methyl group, and X is a fluorine or methoxy group such that R is hydrogen only when X is fluorine, and its acid addition salts;

(2) A therapeutic method of treating hypertension in an individual for whom such therapy is indicated, comprising; administering a therapeutically effective amount of a compound having Formula I to the individual;

(3) A process for preparing a compound having Formula I wherein R is a hydrogen atom, comprising:
(a) reacting a compound having Formula II,

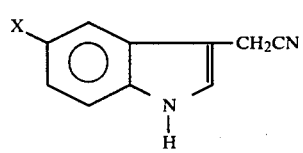

wherein X is a fluorine or methoxy group, with an alkali metal base and an acyloxylating agent to produce a compound having Formula III;

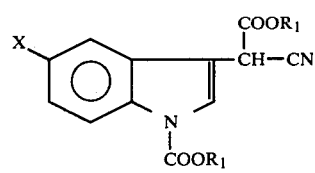

wherein X is as above and $R_1$ is a lower alkyl or aryl group;

(b) hydrogenating the compound having Formula III in the presence of a catalyst to produce a compound having Formula IV,

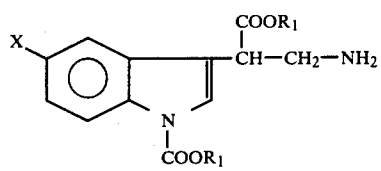

and $R_1$ and X are as above;

(c) hydrolyzing the compound having Formula IV with an aqueous alkali metal hydroxide to produce a compound having Formula V

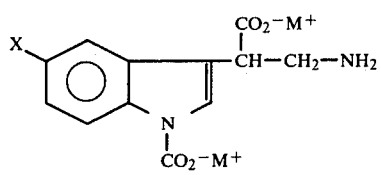

wherein $M^+$ is an alkali metal cation and X is as defined above; and (d) decarboxylating the compound having Formula V with an aqueous acid and isolating the desired product.

(4) A process for preparing a compound having Formula I, wherein R is a methyl group, comprising: esterifying the compound produced in Part 3d above with methanol in the presence of an acid catalyst; and (5) The intermediate, 3-amino-2-(5-methoxy-1H-indol-3-yl) propanoic acid, useful in the preparation of compounds having Formula I.

DESCRIPTION OF THE INVENTION

The novel compounds having Formula I are the subject of this invention. In compounds having Formula I,

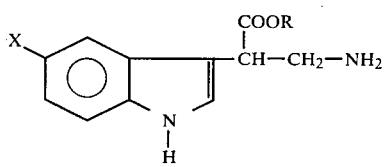

R is a hydrogen or methyl group, and X is a fluorine or methoxy group such that R is hydrogen only when X is fluorine.

The invention also includes pharmacologically acceptable acid addition salts of compounds having Formula I. Such salts are prepared from suitable acids, such as hydrochloric, hydrobromic, maleic, fumaric, or the like. The acid addition salts are prepared by reacting compounds of Formula I with at least one equivalent of acid in a water-polar organic solvent mixture, such as water and ethanol.

The compounds and salts of this invention possess unexpected pharmacological properties that render them useful as therapeutic agents for the treatment of hypertension in an individual for whom such therapy is indicated. In the process of lowering blood pressure the instant compounds produce no tachycardia. The term "individual" means a human being or an experimental animal that is used as a model for a human being. The effective dose may vary from individual to individual, but it is easily determined by one skilled in the art without undue experimentation. Dose forms for the administration of compounds having Formula I may be prepared by recognized methods in the pharmaceutical sciences. Various dose forms of compounds having Formula I may be administered by conventional known methods of therapeutic administration such as oral, intravenous, parenteral, or the like.

The process for preparing compounds having Formula I begins by reacting a compound having Formula II

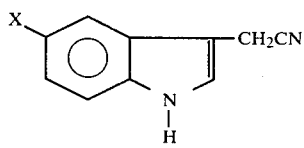

with an alkali metal base and an acyloxylating agent to produce a compound having Formula III,

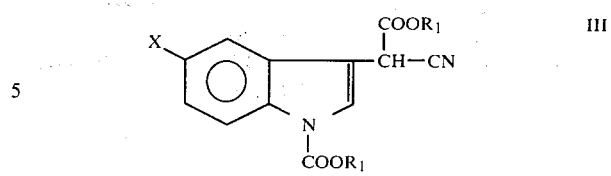

In Formulas II and III, X is a fluorine atom or a methoxy group. The compound having Formula II where X is fluorine is novel, but can be prepared as described in Example 2A below. In Formula III, $R_1$ is a lower alkyl, aryl group or the like. Lower alkyl groups have from 1 to 3 carbon atoms and aryl groups include benzyl, phenyl and the like.

The alkali metal base used in this reaction may be sodium metal, lithium hydride, sodium ethoxide, potassium t-butoxide, or the like. This reaction may be performed in a suitable solvent, such as benzene, dimethylformamide, dimethoxyethane, or the like; or the solvent may be an acyloxylating agent, such as diethyl carbonate, dimethyl carbonate, dibenzyl carbonate or the like. The acyloxylating agent may be one of the carbonates indicated in the previous sentence, or ethyl chloroformate, methyl chloroformate, or the like.

The molar ratios of the compound having Formula II to alkali metal base to acyloxylating agent preferably range from about 1:2:2 to 1:2:10, respectively, with the latter ratio preferred. The preferred reagents are sodium metal and diethyl carbonate, wherein the latter acts as both solvent and acyloxylating agent. The reaction takes place in the temperature range of about 0° C. to 110° C., but it is preferred to have the temperature near 110° C. in order to drive the reaction to completion by distilling off a by-product of the reaction, e.g. ethanol.

The compound having Formula III is hydrogenated to convert the cyano group into an aminomethyl group and produce a compound having the Formula IV

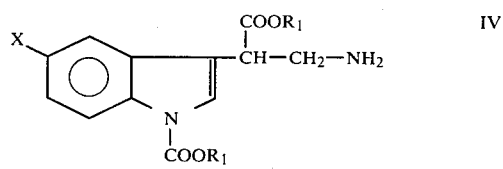

wherein X and $R_1$ are as above. This reduction is performed under pressure in the presence of a catalyst, such as Raney nickel, Palladium on charcoal, Rhodium on charcoal, or the like. Raney nickel is preferred. The reduction is preferably carried out in a suitable solvent such as methanol, ether, dimethylformamide, or the like at a temperature from about 15° C. to 60° C. Certain acylating agents may act as solvents also, as further described below.

It should be noted that certain undesirable side reactions may occur during the hydrogenation step above. These side reactions can be preferably avoided by protection of the amine group with an acylating agent. The hydrogenated compound above reacts with an acylating agent to produce the N-acylated compound having the Formula,

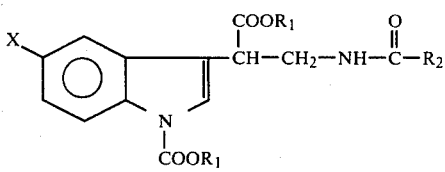

wherein X and $R_1$ are as above, and $R_2$ is a lower alkyl or aryl group. The acylation is performed by reacting a compound having Formula IV with an acylating agent, such as acetyl chloride, acetic anhydride, propionyl chloride, benzoyl chloride, or the like, in a solvent such as ether, dimethylformamide, acetic anhydride, or the like, at a temperature from about 0° to about 60° C.

It should be recognized by those skilled in the art that if acylation is required for protection then the separate reactions of hydrogenation and acylation can also be accomplished in one step. For example, our preferred mode combines the hydrogenation and acylation reactions and most preferably utilizes acetic anhydride as both the solvent for hydrogenation and the acylating agent.

The compound having Formula IV is then hydrolyzed to produce an alkali salt having the Formula V,

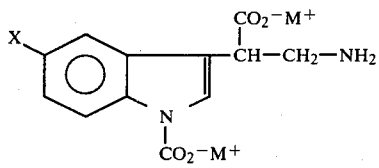

wherein M is an alkali metal cation, with an aqueous solution of an alkali metal hydroxide, such as sodium hydroxide, potassium hydroxide, barium hydroxide, or the like, at a concentration from about 3 N to 10 N for about 1 to 15 hours, at a temperature from about 50° C. to 100° C. The salt is not isolated, but is then promptly decarboxylated to the free acid having Formula I wherein R is hydrogen by addition of an aqueous acid, such as hydrochloric acid, sulfuric acid, or the like. The compound having Formula I wherein R is hydrogen is isolated, after the acidic solution is neutralized, filtered and concentrated.

The compound having Formula I, wherein R is hydrogen, is then esterified by reacting it with methanol in the presence of an acid catalyst, such as hydrochloric acid, sulfuric acid, sulfonyl chloride or the like, and the product, having Formula I, wherein R is methyl, is isolated by convenient means such as preferably crystallization.

EXAMPLE 1

This Example illustrates the preparation of methyl 3-amino-2-(5-methoxy 1H-indol-3-yl) propanoate and also describes the preparation of intermediates.

A. Ethyl 2-cyano-2-(1-ethoxycarbonyl-5-methoxy-1H-indol-3-yl)acetate(Compound 1A)

A vigorously stirred solution of 5-methoxyindole-3-acetonitrile (22.7 g, 0.13 mole; prepared as described by JUBY and HUDYMA J. Med. Chem. 12, 396 (1969)) in 200 ml of diethylcarbonate was heated at 110° C. and sodium (6.0 g, 0.26 mole) was added in small pieces over a 30 minute period, during which time ethanol distilled off. The mixture was kept at 110° C. for an additional 60 minutes, and the excess solvent removed in vacuo. The remaining mixture was cooled to about 20° C. and a dilute solution of acetic acid (18 ml glacial acetic acid in 100 ml of water) was added thereto. Then 200 ml of ethyl acetate was added, and the mixture stirred until all solids had dissolved. The organic portion of this mixture was separated, washed with brine, dried over $MgSO_4$, and the solvent evaporated in vacuo to leave a dark residue. This residue was chromatographed on Silica Gel 60 with benzene:ethyl acetate (9:1 v:v) solvent and the solvent evaporated in vacuo to isolate compound 1A above as a light yellow syrup. The product was crystallized from methanol; yield 20 g (47%), mp 81°–83° C.

Anal. Calcd. for $C_{17}H_{18}N_2O_5$: C,61.81; H,5.49; N,8.48, Found: C,62.37; H,5.58; N,8.55.

B. Ethyl 3-acetylamino-2-(1-ethoxycarbonyl-5-methoxy-1H-indol-3-yl)propanoate (TR-3328)

A solution of Compound 1A, prepared above, (7.4 g, 0.022 mole) in 150 ml of acetic anhydride was hydrogenated for 20 hours at 50 psi, using about 10 g of Raney nickel as a catalyst. The catalyst was then removed by filtration, and the solvent was evaporated in vacuo to leave a thick syrup. This syrup was dissolved in 200 ml of ethyl acetate which was then washed five times with 6% aqueous potassium carbonate solution and dried over $MgSO_4$. The solvent was then evaporated in vacuo, and the syrup which remained was crystallized from ethyl acetate:petroleum ether. One recrystallization from the same solvent pair yielded 4.6 g (56%) of product, mp. 88°–90° C.

Anal. Calcd. for $C_{19}H_{24}N_2O_6$: C,60.62; H,6.43; N,7.44, Found: C,60.93; H,6.70; N,7.87.

C. 3-Amino-2-(5-methoxy-1H-indol-3-yl)propanoic acid (TR-3361)

A mixture of TR-3328 (5.3 g, 0.014 mole; prepared in Part 1B above) and 18 ml of 10 N NaOH was heated at reflux temperature for 8 hours. The mixture was diluted with 100 ml of water, powdered charcoal was added, and the resulting mixture stirred and filtered to produce a clear filtrate. The filtrate was acidified to pH 6.0 with acetic acid, diluted to 200 ml with water, heated to boiling, treated with powdered charcoal, filtered, concentrated in vacuo until solid material was seen, and cooled at about 4° C. for 16 hours. The solid was then removed by filtration, recrystallized from water, and dried over $P_2O_5$; yield 2.1 g (64%), mp 205°–207° C. dec.

Anal. Calcd. for $C_{12}H_{14}N_2O_3$: C,61.52; H,6.02; N,11.96, Found: C,60.58; H,6.27; N,11.82.

D. Methyl 3-Amino-2-(5-methoxy-1H-indol-3-yl)propanoate Hydrochloride (TR-3369)

A stirred suspension of TR-3361 (1 g, 0.0043 mole, prepared in Part 1C, above) in 8 ml of methanol was cooled to $-10°$ C. and $SOCl_2$ (0.4 ml, 0.0056 mole) was added dropwise to generate a clear yellow solution. This solution was stirred for 18 hours at 18° C., and the solvent was then removed in vacuo to leave a gummy residue which turned into a solid upon trituration with ethyl acetate. The residue was partitioned between ethyl acetate and 6% $K_2CO_3$ solution. The organic phase was washed once with brine, dried over MgSO$_4$, and 1.1 ml of 4 N HCl (in dioxane) was added to produce a precipitate. The solid was removed by filtration and dried over P$_2$O$_5$ to yield 0.8 g product (67%), m.p.

Anal. Calcd. for C$_{13}$H$_{17}$N$_2$O$_3$Cl: C,54.83; H,6.02; N,9.84 Cl,12.45, Found: C,54.36; H,6.23; N,9.54 Cl,12.21.

EXAMPLE 2

This example describes the preparation of 3-amino-2-(5-fluoroindol-3-yl)propanoic acid and its intermediates

A. 5-Fluoroindole-3-acetonitrile

A mixture of 38 g of 3-dimethylaminomethyl-5-fluoroindole (0.198 mole; cf. Hoffman et al. J. Heterocyclic Chem. 2, 298 (1965); of the 5-fluorogramine therein) in 500 ml of methanol was prepared. Then a solution of 25.7 g of KCN (0.396 mole) in 50 ml of water was added, with stirring. The stirred mixture was cooled to 20° C. and 34.6 ml of methyl iodide (0.556 mole) was added over a 20 minute period. The mixture was then stirred at about 20° C. for 16 hours. The solvent was removed by evaporation and the residue was partitioned between ether and water. The ether portion was washed with water, 5% HCl, saturated NaHCO$_3$ solution, water, and brine, dried over MgSO$_4$ and evaporated to leave a liquid residue. This residue was distilled at reduced pressure in a Kugelrohr apparatus. The fraction distilling at 134°–140° C. and 0.3 to 0.1 Torr was collected and crystallized from ethyl acetate-petroleum ether, mp 58°–59°, yield 5.3 g (44%).

B. Ethyl 2-cyano-2-(1-ethoxycarbonyl-5-fluoroindol-3-yl)acetate (Compound 2B)

A stirred solution of 5-fluoroindole-3-acetonitrile (15.3 g; 0.88 mole; prepared in Part 2A above) in 250 ml of diethylcarbonate was heated at 110° C. and sodium (4.0 g; 0.17 mole) was added in small pieces. The mixture was then kept at 110° C. for an additional 30 minutes, during which time ethanol distilled off. The excess solvent and ethanol was then removed in vacuo. The residue that remained was cooled and to it was added a dilute solution of acetic acid (25 ml of glacial acetic acid in 100 ml of water). This aqueous mixture was extracted with two 100 ml portions of ether, which were combined, dried over MgSO$_4$ and evaporated to leave a syrup. This syrup crystallized when triturated with methanol. The yield of product was 17 g (61%).

C. Ethyl 3-acetylamino-2-(1-ethoxycarbonyl-5-fluoroindol-3-yl) propanoate (Compound 2C)

A solution of Compound 2B, (17 g, 0.054 mole; prepared in Part 2B above) in 250 ml of acetic anhydride was hydrogenated as in Example 1B, and the crystalline product isolated following the procedure therein. The product melted at 120°–121° C.; the yield was 9 g (46%).

Anal. Calcd. for C$_{18}$H$_{21}$FN$_2$O$_5$: C,59.32; N,7.69; H,5.81, Found: C,59.05; N,7.54; H,5.82.

D. 3-Amino-2-(5-fluoro-1H-indol-3-yl)propanoic acid (TR-3913)

A 4.5 g (0.017 mole) sample of the Compound 2C, prepared in Part 2C above, was hydrolyzed as described in Example 1C above. Isolation of the crystalline product (2 g (72%), mp 244°–245° C.) was accomplished by the procedure therein.

Anal. Calcd. for C$_{11}$H$_{11}$FNO$_2$: C,59.46; H,4.99; N,12.61, Found: C,58.67; H,4.96; N,12.89.

EXAMPLE 3

Methyl 3-amino-2-(-5-fluoro-1H-indol-3-yl) propanoate hydrochloride TR-3915)

The methyl ester of TR-3913 was prepared as described in Example 1D, except TR-3913 (1.6 g, 0.007 mole) was utilized in place of TR-3361 and 0.74 ml of thionyl chloride (0.010 mole) was used. TR-3915, mp 186°–187° C., was isolated in 63% yield (1.2 g).

Anal. Calcd. for C$_{12}$H$_{14}$FN$_2$O$_2$Cl: C,52.85; H,5.17; N,10.27, Found: C,52.71; H,5.16; N,10.04.

EXAMPLE 4

This example describes the results obtained when the compounds of this invention and reference compounds were tested for their ability to lower blood pressure in hypertensive rats.

Rats were made hypertensive by applying a figure-of-eight ligature to one kidney and removing the other kidney two weeks later. At least four weeks elapsed, after the second operation, before experimental studies were performed. Indirect systolic blood pressure measurements were made with an occluding cuff and pulse sensor system fitted to the rats' tails. Control blood pressure measurements were made before any compounds were administered. Blood pressure measurements were then made 1,2,4,6, and 8 hours after the oral administration of the test compounds at the dose level of 10 mg/kg. Compounds 1D, 2D and 3 were tested in 10 rats and reference compounds A and B were tested in 5 rats. Statistical significance of differences between control and post-treatment values was determined by Wilcoxon's signed rank test (F. Wilcoxon and R. A. Wilcox, Some Rapid Approximate Statistical Procedures, Lederle Laboratories, Pearl River, 1964).

The results of the tests are given in the table below.

| | Changes in rat blood pressure (mm Hg) upon oral administration of test compound | | | | | | |
|---|---|---|---|---|---|---|---|
| Example | Compound | mg/kg | 1 hr | 2 hr | 4 hr | 6 hr | 8 hr |
| 1D | TR-3369 | 3 | −43* | −36* | −18* | 0 | −3 |
| 1D | TR-3369 | 10 | −85* | −71* | −38* | −10 | +2 |
| 2D | TR-3913 | 10 | −19* | −26* | −27* | −15 | 0 |
| 3 | TR-3915 | 10 | −28* | −18* | −9 | −4 | −1 |
| | References Compound A | 10 | −9 | −6 | 0 | +6 | −1 |
| | References Compound B | 10 | −2 | −7 | +14 | +22* | +6 |

*Statistically significant ($p < 0.05$)
Reference Compound A refers to 5-hydroxy tryptophan.
Reference Compound B refers to α-methyl, 5-hydroxy tryptophan ethyl ester.

The data above clearly shows that the claimed compounds are useful for lowering blood pressure in a hypertensive animal and have an especially long duration of action. By comparison with Reference compounds A and B, reported to lower blood pressure, the claimed compounds are dramatically more active and especially over a longer period of time.

We claim:

1. A process for preparing a compound having Formula I

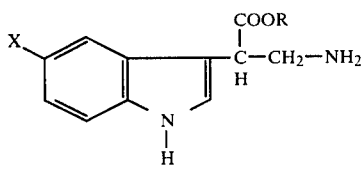

I wherein R is a hydrogen atom or a methyl group and X is fluorine or a methoxy group, comprising the steps of:
(a) reacting a compound having Formula II

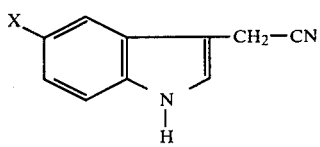

II wherein X is fluorine or a methoxy group, with an alkali metal base selected from the group of sodium metal, lithium hydride, sodium ethoxide or potassium t-butoxide and an acyloxylating agent selected from the group of diethyl carbonate, dimethyl carbonate, dibenzyl carbonate, ethyl chloroformate or methyl chloroformate in a suitable solvent at a temperature in the range of from about 0° to 110° C. to produce a compound having Formula III

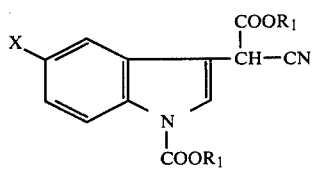

III wherein X is as above and $R_1$ is a lower alkyl group of from 1 to 3 carbon atoms or a phenyl group;
(b) separating compound III from the reaction mass;
(c) hydrogenating the compound having Formula III under pressure, in the presence of a catalyst, in a suitable solvent selected from the group of acetyl chloride, acetic anhydride, propionyl chloride or benzoyl chloride to produce a compound having Formula IV,

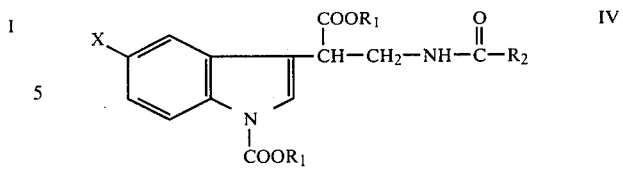

IV wherein $R_1$ and X are as defined above and $R_2$ is methyl, ethyl or phenyl;
(d) separating Compound IV from the reaction mass;
(e) hydrolyzing the compound having Formula IV with an aqueous alkali metal hydroxide at a concentration from about 3 N to 10 N for about 1 to 15 hours, at a temperature of from about 50° C. to 100° C. to produce a compound having Formula V,

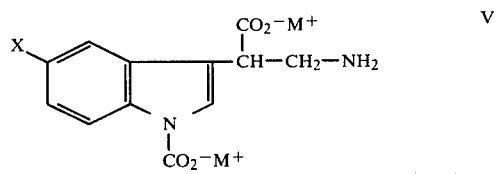

V wherein $M^+$ is an alkali metal cation and X is as defined above;
(f) decarboxylating the compound having Formula V with an aqueous acid at a temperature from about 50° C. to 100° C. and isolating the compound having Formula I wherein R is a hydrogen atom and X is as defined above, and
(g) optionally esterifying the compound having Formula I, wherein R is a hydrogen atom and X is as defined above, with methanol in the presence of an acid catalyst to produce the compound having Formula I wherein R is a methoxy group and X is as defined above.

2. The process of claim 1 wherein the acylating agent is acetic anhydride.
3. The process of claim 1 wherein the catalyst is Raney Nickel, Palladium on Charcoal or Rhodium on Charcoal.
4. The process of claim 3 wherein the catalyst is Raney nickel.
5. The process of claim 1 wherein the ratios of compound having Formula II to alkali metal base to acyloxylating agent in step (a) on a molar basis range from about 1:2:2 to 1:2:10 respectively.

* * * * *